United States Patent
Beets et al.

(10) Patent No.: US 7,873,142 B2
(45) Date of Patent: Jan. 18, 2011

(54) DISTORTION CORRECTION METHOD FOR LINEAR SCANNING X-RAY SYSTEM

(75) Inventors: Matthew Paul Beets, Rondebosch (ZA); Frederick Charles Nicolls, Cape Town (ZA); Gerhardus De Jager, Newlands (ZA)

(73) Assignee: Lodox Systems (Proprietary) Limited, Kramerville, Sandton (ZA)

( * ) Notice: Subject to any disclaimer, the term of this patent is extended or adjusted under 35 U.S.C. 154(b) by 27 days.

(21) Appl. No.: 12/475,066

(22) Filed: May 29, 2009

(65) Prior Publication Data
US 2009/0296880 A1 Dec. 3, 2009

Related U.S. Application Data

(60) Provisional application No. 61/057,602, filed on May 30, 2008.

(51) Int. Cl.
*G01N 23/04* (2006.01)
(52) U.S. Cl. .......................... 378/62; 378/4; 378/98.12; 378/146
(58) Field of Classification Search .................. 378/4, 378/62, 98.12, 146, 901; 382/131
See application file for complete search history.

(56) References Cited

U.S. PATENT DOCUMENTS

| | | | |
|---|---|---|---|
| 4,630,203 A * | 12/1986 | Szirtes | 382/132 |
| 6,028,907 A * | 2/2000 | Adler et al. | 378/4 |
| 6,393,090 B1 * | 5/2002 | Hsieh et al. | 378/4 |
| 6,921,200 B1 | 7/2005 | Booysen et al. | |
| 7,519,143 B2 * | 4/2009 | Debasish et al. | 378/7 |

FOREIGN PATENT DOCUMENTS

WO WO 00/53093 A1 9/2000

OTHER PUBLICATIONS

Bortfeld, et al. "Fast and exact 2D image reconstruction by means of Chebyshev decomposition and backprojection," Phys. Med. Biol., vol. 44, 1999, pp. 1105-1120.*

* cited by examiner

*Primary Examiner*—Edward J Glick
*Assistant Examiner*—Thomas R Artman
(74) *Attorney, Agent, or Firm*—Buchanan Ingersoll & Rooney PC

(57) ABSTRACT

Imaging apparatus comprises a radiation source arranged to generate a divergent imaging beam and an associated radiation detector mounted on a C-arm which can rotate. A first drive is arranged to move the radiation source and the detector relative to a subject in a scanning direction to generate output signals from the detector, thereby performing a scan generating image data containing distortion in a direction transverse to the scanning direction. A second drive is arranged to rotate the C-arm, to change the orientation of the radiation source in a direction transverse to the scanning direction incrementally between repeated scans, thereby to generate a plurality of sets of image data. A processor, which can be a PC or a dedicated processor, is provided for processing each set of image data to obtain equivalent parallel imaging beam data therefrom, corresponding to a given angle in the divergent imaging beam, and for combining a plurality of said equivalent parallel imaging beam data to generate a synthesized parallel imaging beam image. The apparatus includes a display for generating a visual display of the synthesized parallel imaging beam image. The resulting synthesized image has the distortion removed and measurements can be made from the image. The invention extends to a method carried out with the apparatus.

12 Claims, 17 Drawing Sheets

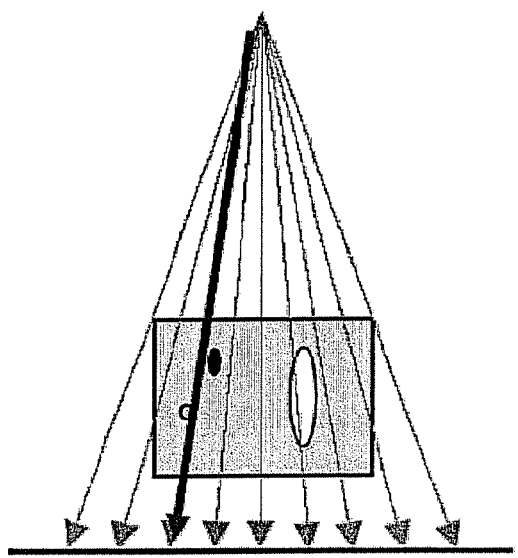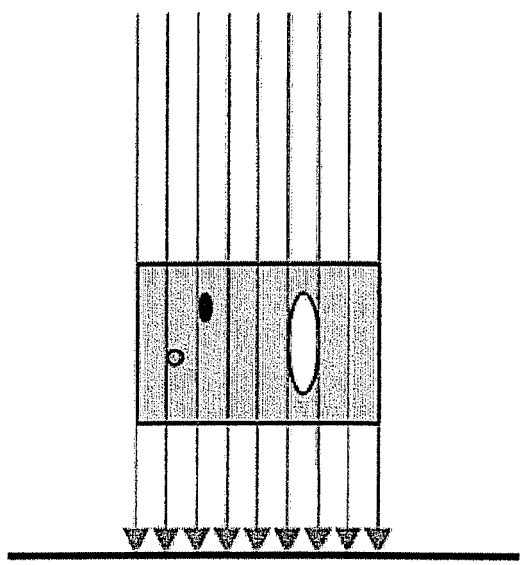
Fig. 6(a)　　　　　　　　Fig. 6(b)
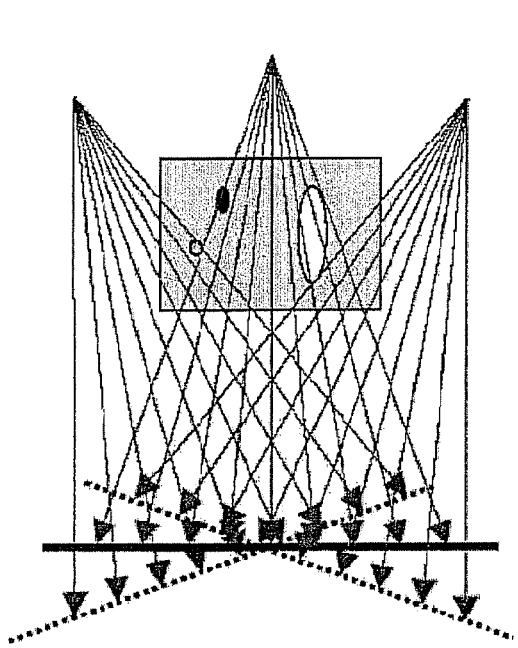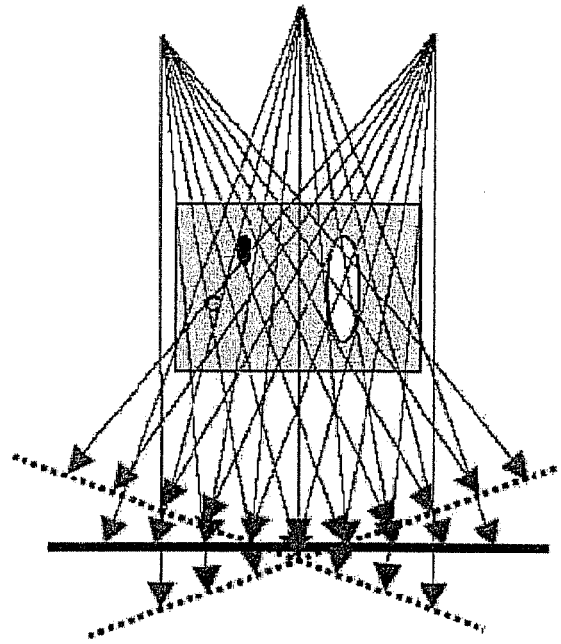
Fig. 7(a)　　　　　　　　Fig. 7(b)

Position along axis

DISTORTION CORRECTION METHOD FOR LINEAR SCANNING X-RAY SYSTEM

BACKGROUND OF THE INVENTION

This invention relates to a method of correcting distortion in a linear scanning X-ray system, and to apparatus for implementing the method.

Linear scanning X-ray systems are known which comprise a radiation source mounted at one end of a C-shaped arm for generating an imaging beam, a detector at an opposed end of the C-arm responsive to the imaging beam to generate an output signal, and a drive arranged to move at least one of the radiation source and the detector relative to a subject in a scanning direction. Such systems are typically used for the acquisition of whole-body images of a patient or other subject, as described in U.S. Pat. No. 6,921,200 or International patent application no. WO 00/53093.

For example, such apparatus can be used provide fast X-ray images of injured patients. Once a patient has been stabilized, he or she can conveniently be placed on a trolley or gurney, placed in position, scanned, and wheeled out for further treatment, with the resulting radiograph appearing on the diagnostic screen virtually instantaneously. Due to the low X-ray dose administered by the apparatus, the risk of radiation exposure to staff and patients is reduced.

X-ray images from such apparatus contain a non-linear distortion that must be corrected for critical applications. This distortion is a result of the imaging process: X-rays from a point source are spread out into a fan beam before being captured by a detection device such as a photographic plate or an electronic CCD sensor.

Because of this, objects closer to the centre of the detector suffer less distortion than those at the edges. This makes the correction process a non-trivial task, traditionally requiring multiple scans to be taken and stitched together manually to minimise the distortion. The distortion correction of X-ray images is of particular interest in certain medical fields, particularly for prosthetics, implants, and orthopaedic work.

It would be desirable to be able to take accurate measurements directly from X-ray images, and that these images should be obtained with a minimum of patient discomfort and exposure to radiation.

SUMMARY OF THE INVENTION

According to the invention there is provided a method of operating imaging apparatus of the kind having a radiation source and an associated radiation detector which are moveable relative to a subject, the method comprising:
(a) generating a divergent imaging beam from the radiation source;
(b) moving the radiation source and the radiation detector relative to a subject in a scanning direction to generate output signals from the detector, thereby generating image data from the detector containing distortion in a direction transverse to the scanning direction;
(c) changing the orientation of the radiation source in a direction transverse to the scanning direction and repeating step (b) one or more times to generate a plurality of sets of image data;
(d) processing each set of image data to obtain equivalent parallel imaging beam data therefrom, corresponding to a given angle in the divergent imaging beam; and
(e) combining a plurality of said equivalent parallel imaging beam data to generate a synthesized parallel imaging beam image.

The divergent imaging beam will typically be a fan shaped imaging beam generated by a linear scanning apparatus.

The fan shaped imaging beam is preferably relatively narrow in the scanning direction and relatively wide in a direction transverse to the scanning direction.

Changing the orientation of the radiation source in a direction transverse to the scanning direction may comprise rotating the radiation source and detector about an axis extending parallel to the scanning direction at selected angular intervals.

The linear scanning apparatus may comprise a support member which supports the radiation source and the associated radiation detector for rotation about an axis which extends parallel to the scanning direction, but which is offset relative to a midline of the fan shaped imaging beam, the method including the step of processing the image data to re-project the image data so that it represents a virtual fan shaped imaging beam having a midline that coincides with the axis of rotation of the support member.

The image data preferably defines a multi-line image, the method comprising generating a set of sinograms from the image data, each sinogram representing angular views at a specified line of the image, re-projecting the sinogram data from a fan bean to a parallel beam format, constructing a set of new sinograms consisting of virtual parallel beam data, and reconstructing a virtual parallel beam image from the virtual parallel beam data at a selected angle of view.

Further according to the invention there is provided Imaging apparatus comprising:
(a) a radiation source arranged to generate a divergent imaging beam and an associated radiation detector;
(b) a first drive arranged to move the radiation source and the detector relative to a subject in a scanning direction to generate output signals from the detector, thereby performing a scan generating image data containing distortion in a direction transverse to the scanning direction;
(c) a second drive arranged to change the orientation of the radiation source in a direction transverse to the scanning direction incrementally between repeated scans, thereby to generate a plurality of sets of image data;
(d) at least one processor for processing each set of image data to obtain equivalent parallel imaging beam data therefrom, corresponding to a given angle in the divergent imaging beam, and for combining a plurality of said equivalent parallel imaging beam data to generate a synthesized parallel imaging beam image; and
(e) a display for generating a visual display of the synthesized parallel imaging beam image.

The imaging apparatus may be a linear scanning apparatus in which the first drive is arranged to move the radiation source and the associated radiation detector along a linear path corresponding to the scanning direction, and wherein the divergent imaging beam is a fan shaped imaging beam.

The fan shaped imaging beam is preferably relatively narrow in the scanning direction and relatively wide in a direction transverse to the scanning direction.

The second drive may be arranged to change the orientation of the radiation source in a direction transverse to the scanning direction by rotating the radiation source and detector about an axis extending parallel to the scanning direction at selected angular intervals.

In one embodiment, the linear scanning apparatus comprises a support member which supports the radiation source and the associated radiation detector for rotation about an axis which extends parallel to the scanning direction, but which is offset relative to a midline of the fan shaped imaging beam, said at least one processor being operable to apply an algorithm to the image data to re-project the image data so that it represents a virtual fan shaped imaging beam having a midline that coincides with the axis of rotation of the support member.

The image data may define a multi-line image, said at least one processor being operable to generate a set of sinograms from the image data, each sinogram representing angular views at a specified line of the image; to reproject the sinogram data from a fan bean to a parallel beam format; to construct a set of new sinograms consisting of virtual parallel beam data; and to reconstruct a virtual parallel beam image from the virtual parallel beam data at a selected angle of view.

BRIEF DESCRIPTION OF THE DRAWINGS

FIGS. 6(a) and (b) are schematic diagrams illustrating the imaging geometry of a fan-beam and a parallel beam linear scan imaging system;

FIGS. 7(a) and (b) are schematic diagrams similar to those of FIG. 6, showing the effect of non-linear and magnification distortion in a fan-beam imaging system;

DESCRIPTION OF PREFERRED EMBODIMENTS

Figure 1:
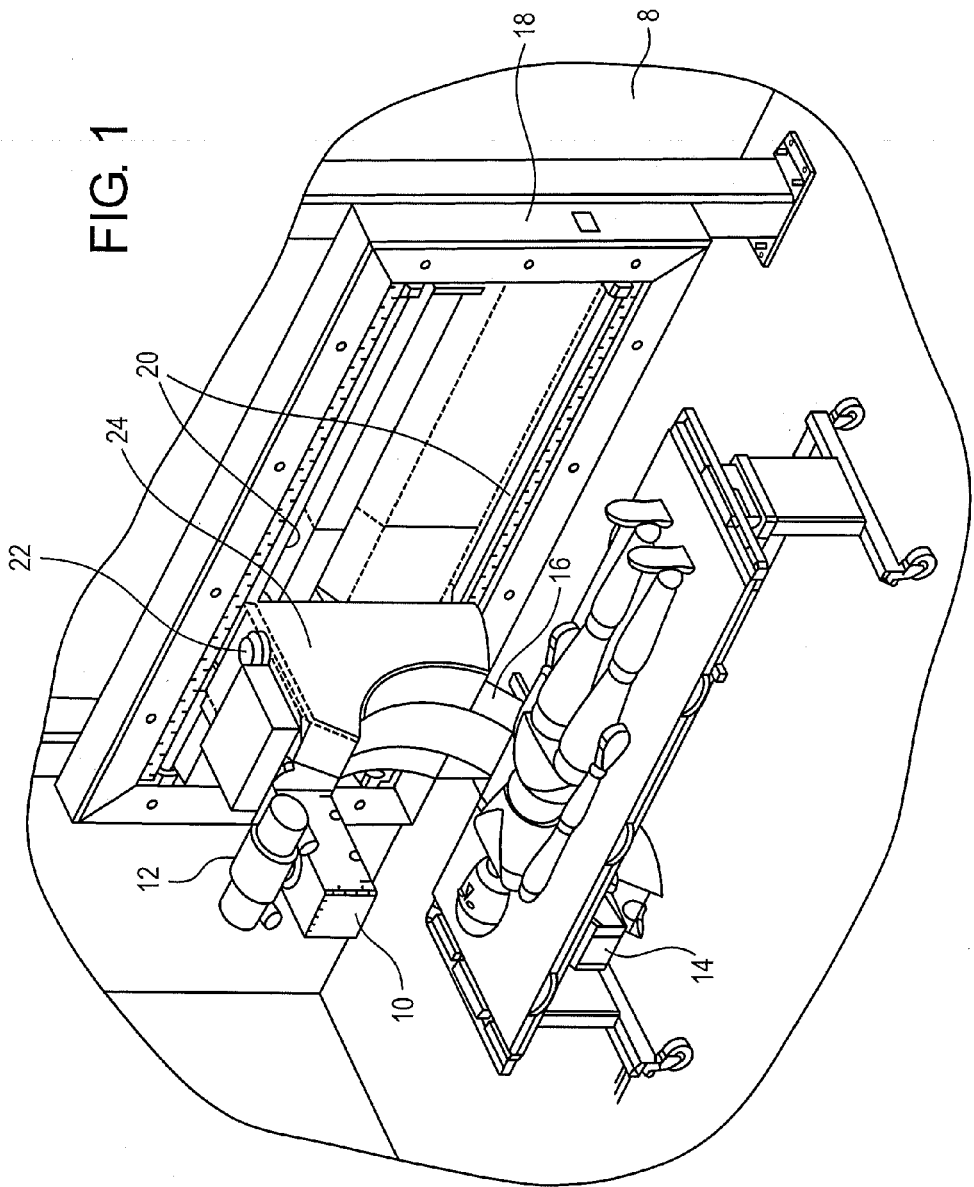
FIG. 1 is a pictorial view of linear scan imaging apparatus usable to implement a distortion correction method according to the invention.
Figure 2:
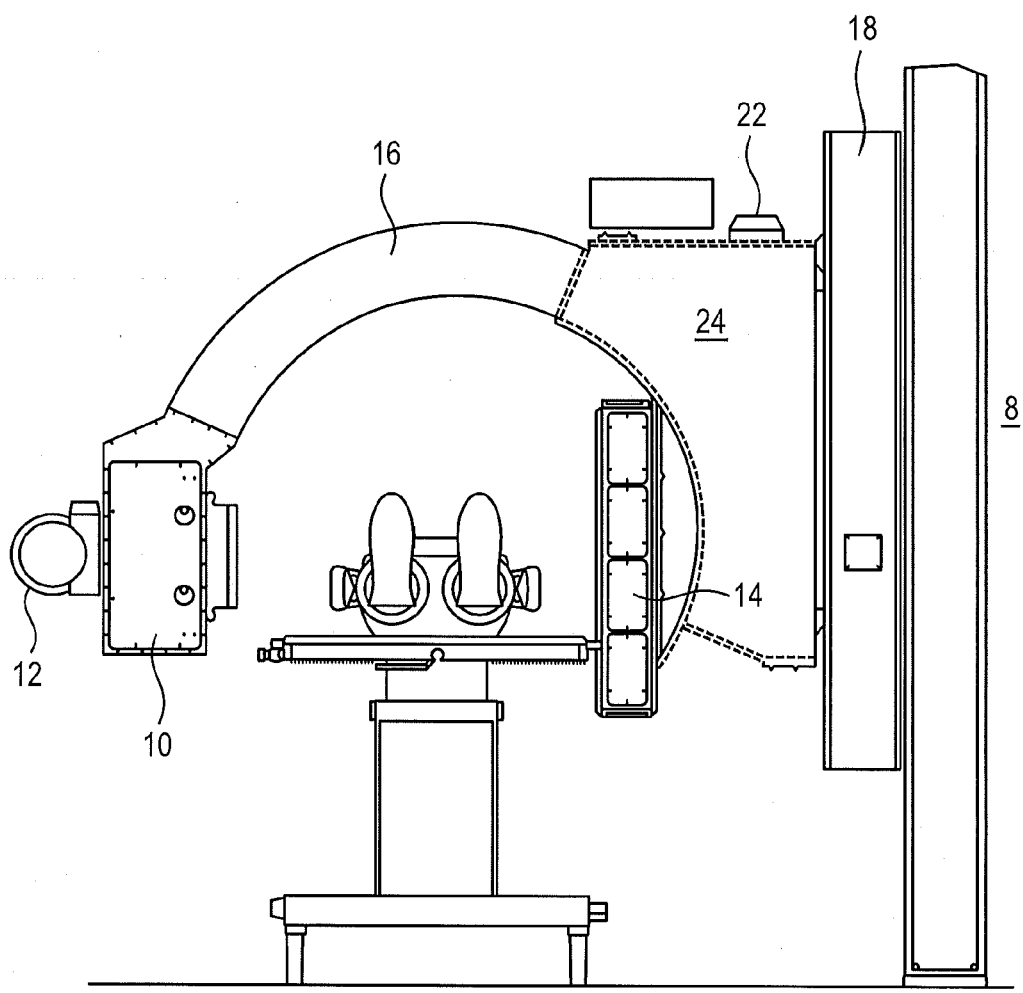
FIG. 2 is an end elevation of the apparatus of FIG. 1 showing a scanning arm thereof rotated through 90°.
Figure 3:
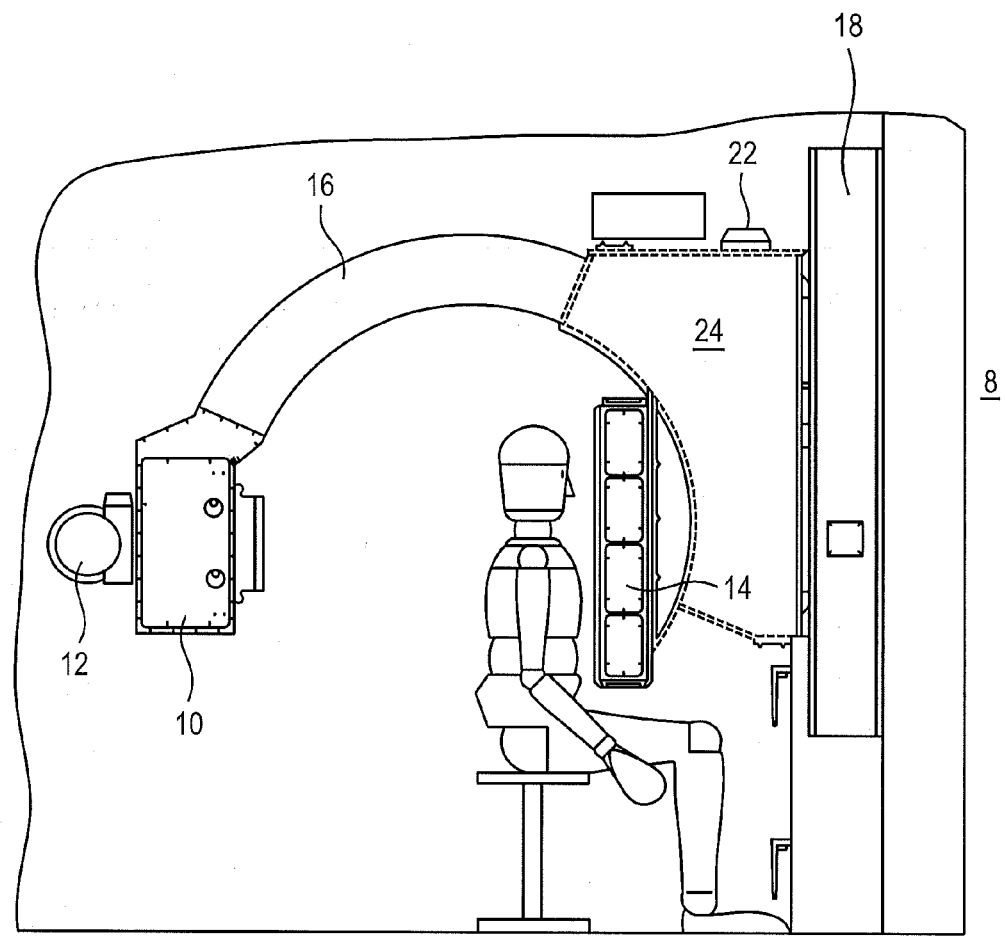
FIG. 3 is a similar view to that of FIG. 2, showing an alternative application of the apparatus.

FIGS. 1 to 3 show three different views of X-ray imaging or scanning apparatus of the kind suitable for implementing the method of the invention. The apparatus comprises a head 10 containing an X-ray source 12 which emits a narrow, fanned beam of X-rays towards a detector unit 14. The X-ray source 12 and the detector unit 14 are supported at opposite ends of a curved arm 16 which is generally semi-circular or C-shaped.

A frame 18 mounted on a wall 8 or another fixed structure defines a pair of rails 20 with which a motorised drive mechanism 22 engages to drive the arm linearly back and forth in a first, axial direction of movement. This corresponds to the direction of scanning in use. In addition, the drive mechanism comprises a housing 24 in which the arm 16 is movable by the drive mechanism in order to cause the X-ray source and the detector to rotate about an axis parallel with the scanning direction of the mechanism.

Figure 4:
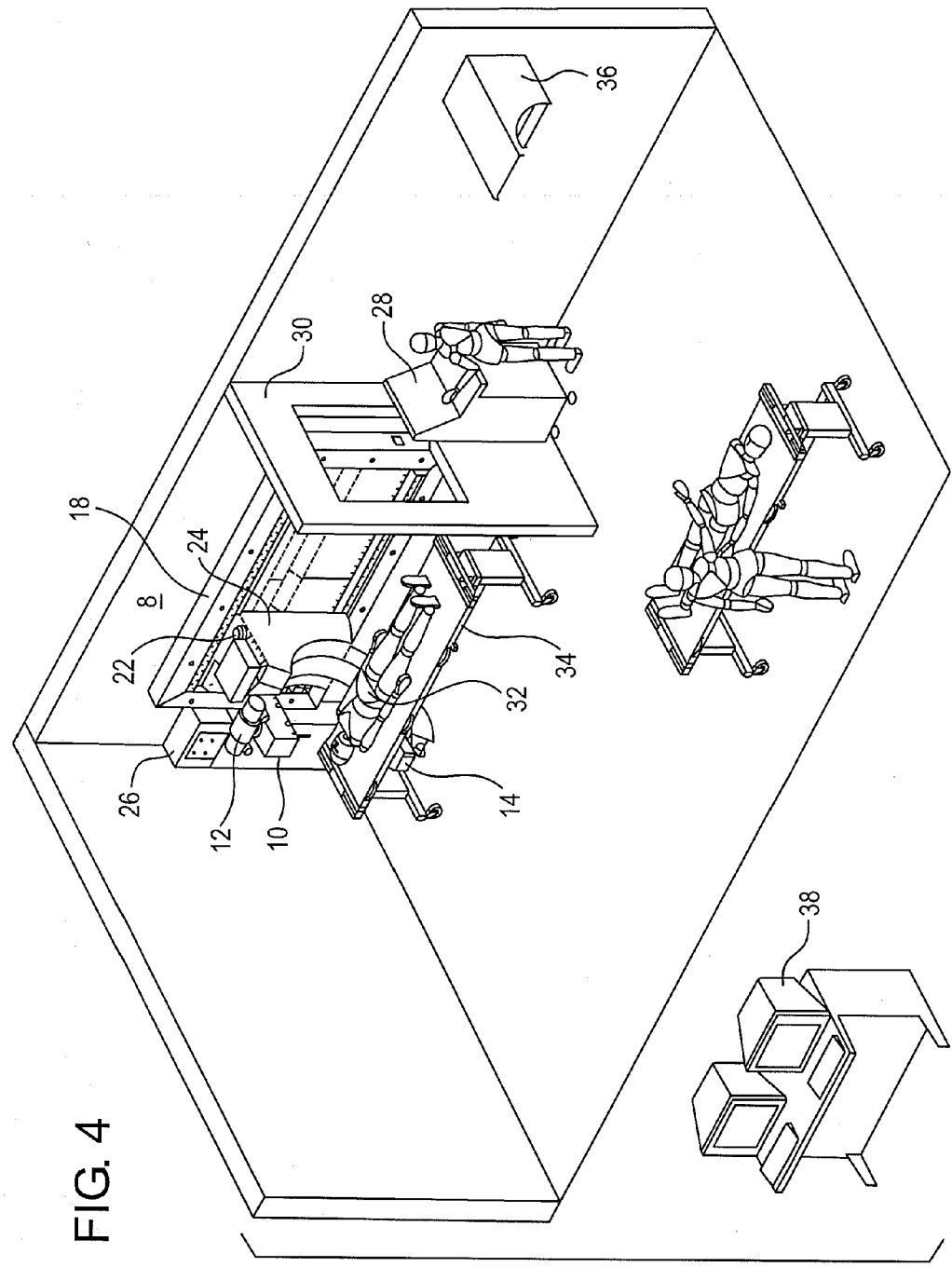
FIG. 4 is a pictorial view of a radiological installation incorporating the apparatus.

A typical application of the imaging apparatus of the invention is in a radiological installation, such as that illustrated in FIG. 4. The imaging apparatus is shown located in a corner of a room which may be a resuscitation area or trauma room of a hospital, for example. Alternatively, the apparatus may be located in a radiological department of a hospital or elsewhere. Imaging apparatus as described is manufactured by Lodox under the trade mark STATSCAN.

Located adjacent to the imaging apparatus is a local positioning console 26, by means of which an operator can set up the required viewing parameters (for example, the angle of the arm 16, start and stop positions, and the width of the area to be X-rayed). A main operator console 28 is provided behind a screen 30 which is used by the operator to set up the required radiographic procedure. The imaging apparatus is operated to perform a scan of a subject 32 supported on a specialised trolley or gurney 34 (see below) and an image of the radiograph is displayed on a screen at the console 28, in order to allow the operator to judge whether a successful image has been acquired.

One or more high quality monitors 36 are provided for diagnostic viewing and are located so that attending clinical staff can study the radiographs being acquired. In addition, a console 38 is provided which forms part of a standard Radiological Information System which permits picture viewing and archiving.

The arrangement of FIG. 4 is designed for use in the resuscitation room of a trauma unit, in order to provide fast X-ray images of injured patients. Once a patient has been stabilised, he or she can conveniently be placed in position, scanned, and wheeled out for further treatment, with the resulting radiograph appearing on the diagnostic screen virtually instantaneously. Due to the low X-ray dose administered by the apparatus, the risk of radiation exposure to staff and patients is reduced.

The apparatus described above is generally similar to that described in International patent application no. WO 00/53093, the contents of which are incorporated herein by reference.

Figure 5:
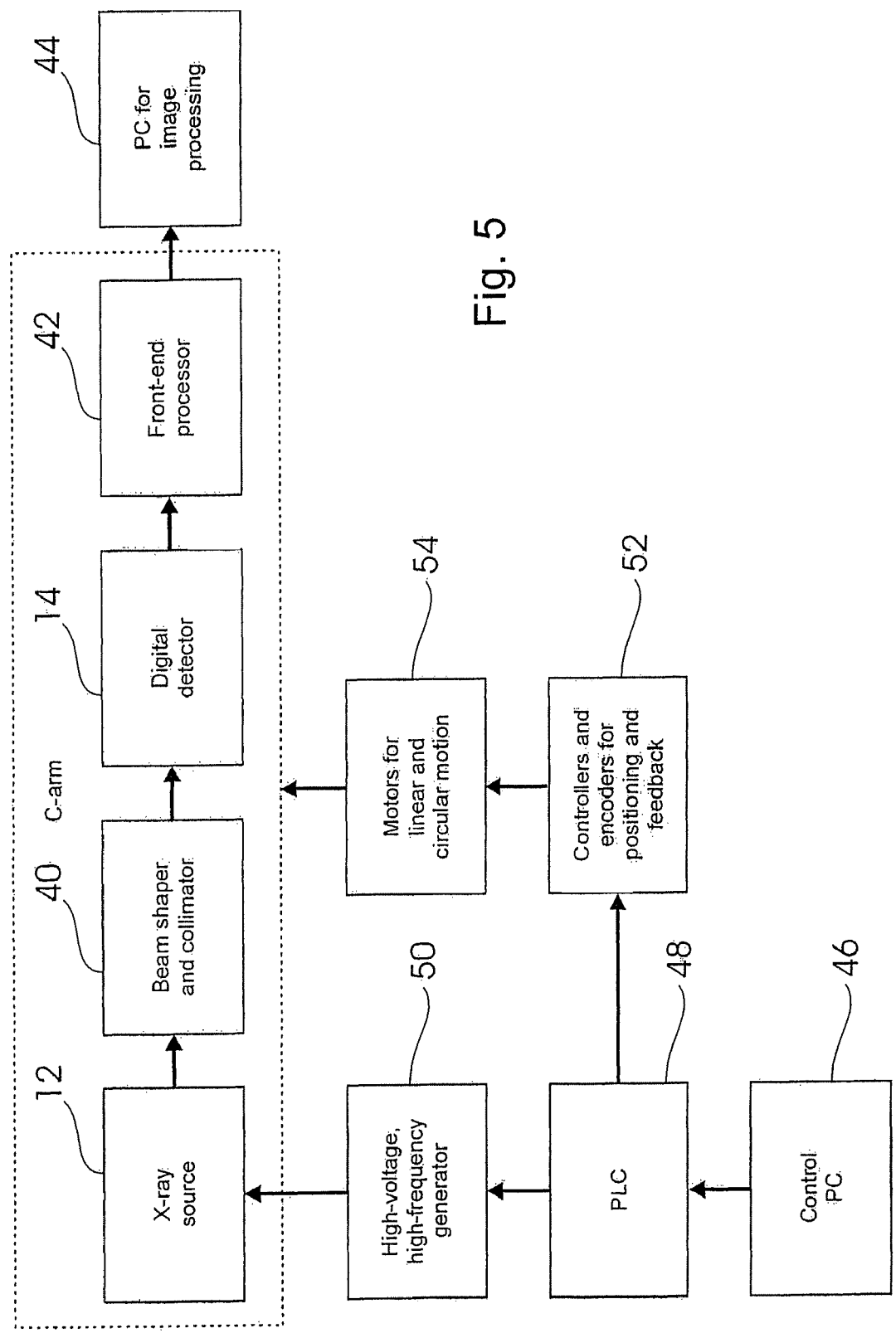
FIG. 5 is a simplified schematic block diagram showing major components of the apparatus.

Referring to the schematic block diagram of FIG. 5, the arrangement of the active components and electronic circuits of the apparatus is shown in a simplified form. Associated with the X-ray source or tube 12 is a beam shaper and collimator 40, which converts the output of the X-ray source to the required fan shape. At the other end of the C-arm 16, the detector 14 has an associated front-end processor 42, which performs the initial processing of the raw image data from the detector. The output of the front-end processor is passed to a PC 44 for image processing.

It will be appreciated that the specific details of the described STATSCAN apparatus are provided by way of example, and that other generally similar apparatus could also be used to generate the necessary image data.

The PC 44 needs to be capable of processing the data received from the front-end processor 42 and be able to run in-house designed image-processing software or other software, preferably with at least 1 GB of RAM. The PC has a hard-drive suitable for storing images for processing or storing the final parallel-projected images, and a viewing station, display screen or monitor to display the images thus processed.

It will be appreciated that instead of a general purpose PC, a dedicated processor with associated memory, hard-drive and peripherals could be used to carry out the necessary processing, storage and display tasks.

The software MATLAB was used to code the algorithms according to the invention that are used for processing the images. Because of the geometry of the Lodox STATSCAN machine used, the code was written from the ground up. MATLAB offers this versatility. However, in a commercial application, C++ or other software would be used because it is compiled and runs faster. The PC 44 also requires suitable software to capture and store the DICOM images from the linear scanning X-ray system for further processing with the algorithms according to the present invention.

The overall operation of the apparatus is by means of a control PC 46, via one or more PLCs or microprocessors 48. The PC 46 provides an interface via which an operator can issue instructions to the apparatus and monitor its operation. The PLC or microprocessors control a high-voltage, high-frequency generator 50, which powers the X-ray source 12, as well as interfacing with several controllers and encoders 52. The encoders are provided on the mechanism of the C-arm to enable accurate measurement and adjustment of the C-arm position, and the controllers operate several motors with associated drives 54 which control the linear and circular or rotary motion of the C-arm in use.

The X-ray source (tube) 12 emits a low-dose an output X-ray beam which is passed to the beam shaper and collimator 40, which provides a collimated fan-beam of X-rays. The X-ray detector unit 14 fixed to the other end of the C-arm 16 comprises a set of scintillator arrays optically linked to respective charge-coupled devices (CCDs). An image is acquired by linearly scanning the C-arm over the length of the subject (patient) 32 with the X-ray source active, whilst continuously reading the output of the detector unit in a mode analogous to "scrolling", thus building up a composite image. The front-end processor 42 passes the output read from the detector unit to the image processing PC 44.

In a prototype system of the above describe type, the individual pixels of the detector unit have a 60-micron size, providing up to 11600 elements along the length of the detector. This defines the width of the area to be scanned. Spatial resolutions of 1.04, 1.67, 2.78 or 4.17 line pairs per millimeter (lp/mm) are selectable. The system can record 14 bits of contrast resolution (>16000 grey scales) which compares favorably to the typically 1000 grey scales that can be detected on a conventional x-ray film under ideal viewing conditions. The C-arm is able to rotate axially around the patient to any angle up to 90 degrees, permitting horizontal-beam, shoot-through lateral, erect and oblique views.

The C-arm travels at speeds of up to 144 mm per second. The device is thus able to rapidly acquire images of part or all of the body of a patient, with a full body scan requiring 13 seconds, and with smaller areas requiring proportionately less time.

As indicated above, the described system makes use of the technological principle sometimes referred to as "slit (or slot) scanning" and in this case, specifically "linear slit scanning". The detector is based on CCD technology running in the so-called "drift scanning", alternatively "TDI" (time-division integration) mode.

The X-rays emitted by the source 12 are highly collimated by a single slit in the beam shaper and collimator 40 that irradiates the detector with a narrow "fan beam" of x-rays. The fan beam is "narrow" (3 mm-6 mm) in the scanning direction and "wide" (~696 mm) in a direction transverse to the scanning direction.

As mentioned above, the divergent fan beam used by the linear scanning apparatus results in distortion of the image in a direction transverse to the scanning direction, as indicated schematically in FIG. 6. The divergent fan-shaped imaging beam of FIG. 6(a) "sees" the relative positions of features of a three-dimensional subject differently from a parallel or non-divergent beam as shown in FIG. 6(b).

In order to deal with the problem, the technique of X-ray computed tomography (CT) can be used. This involves the reconstruction of an object's interior density distribution from its projections (x-ray images taken at different angles). A technique for this is based on the Radon transform and Filtered Back Projection method and typically produces an image of a cross-section of the object.

This cross-sectional imaging technique depicts the shape and location of internal structures with great accuracy and without the ambiguity and distortions (scaling and positioning) that limit the usefulness of traditional X-ray images.

A large amount of projection data is needed to provide an accurate, high-resolution reconstruction for this technique. Projection data that covers 180 degrees is required and the more projections within this range the better the final image quality and resolution. From this projection data, a cross-section of the object being X-rayed can be reconstructed. With enough cross-sections a full 3D volume of the object being scanned can be created. This 3D representation could then be used to create virtual X-ray projections of the object at any angle and measurements could be taken from these.

However, this involves taking multiple projections (scans covering at least 180 degrees) of the object. This increases exposure of the imaged subject to radiation. It is also time consuming and requires a large amount of resources to acquire a complete data set.

In the method of the present invention, a very limited set of projections is made (typically only covering a 5 degree range). This projection data can be used to create a single distortion-free planar X-ray image.

The need for much fewer X-ray projections limits patient exposure and decreases the time needed for the procedure.

X-ray images produced by the STATSCAN machine contain a non-linear distortion in the direction of the spread of the fan-beam of X-rays (i.e. the x-axis, transverse to the direction of scanning or y-axis). The amount and type of distortion suffered depends on the object's vertical and horizontal position within the X-ray beam.

As seen in FIGS. 7(a) and 7(b), if the object is too close to the X-ray source, not all of it will be imaged as it will fall outside of the fan beam of X-rays. The further it is to either side of the midline of the fan beam of X-rays, the greater the non-linear distortion it will suffer. The closer it is to the source of the X-rays the greater the magnification error will be due to the beam's divergence.

The X-ray images produced by the STATSCAN machine produce accurate linear dimensions in the scanning direction (the y-axis) and a distortion in the direction of the spread of the fan beams, transverse to the scanning direction (the x-axis). Thus there is only one axis of distortion to be corrected within the X-ray image produced.

The distortion correction method of the invention makes use of the STATSCAN machine's ability to rotate the C-arm in order to get multiple projections at different angles and combine them to create a single distortion-free X-ray image.

What is required is a conversion of a fan-beam X-ray image (an X-ray image produced through the use of a fan-shaped beam of X-rays scanned along the object of interest at a specific angle) into the equivalent parallel beam X-ray image (an X-ray image produced through the use of parallel beams of X-rays scanned along the object of interest at a specific angle).

The parallel beam X-ray image will be accurate in both the scanning direction and beam width direction (i.e. on both the x and y axes referred to above). This is achieved through a software-based method of combining the information from multiple fan-beam X-ray images.

In a CT scan, multiple projections (covering at least 180 degrees) are combined to create a cross-section of the scanned object. This can then be used to create a 3D volume of the object which can be viewed from any angle. This 3D volume could be used to create a distortion-free planar image. This would be done by re-projecting the 3D volume into a 2D image.

It has been shown that the STATSCAN machine can be used for Computed Tomography. However it is limited by the fact that only 90 degrees worth of projections can be acquired at a time, due to the design of the STATSCAN machine and limits on the rotational capability of the C-arm. The other 90 degrees of projections can be acquired by first rotating the object being scanned. Therefore a CT reconstruction of the object could be created and used to create distortion-free images for measurement.

This approach would be very time consuming. It would be better if the stage requiring the reconstruction of the 3D volume of the object could be skipped and a distortion free image could be created directly. That is what the method of the present invention accomplishes.

Using far fewer than 180 projections (typically five or six) it takes the information from these scans and combines them mathematically into one single distortion-free image.

In order to generate the desired corrected image, a series of fan-beam X-rays of the object of interest is required. These should be taken at small, typically one degree, angular intervals and should be sufficiently many to cover the area of interest. This is determined by the width of the table covered by the object.

The power of the machine should be constant through all scans. The necessary power will be determined by which area or thickness of the object is being scanned.

An exploratory scan is first performed to confirm the object's positioning. Final scan parameters (power and number of scans) are determined from that initial scan.

Before the images can be combined to form the final output some pre-processing corrections are made to simplify further processing steps. These include cropping the images, removing background noise, and aligning them to a control marker.

Figure 8:
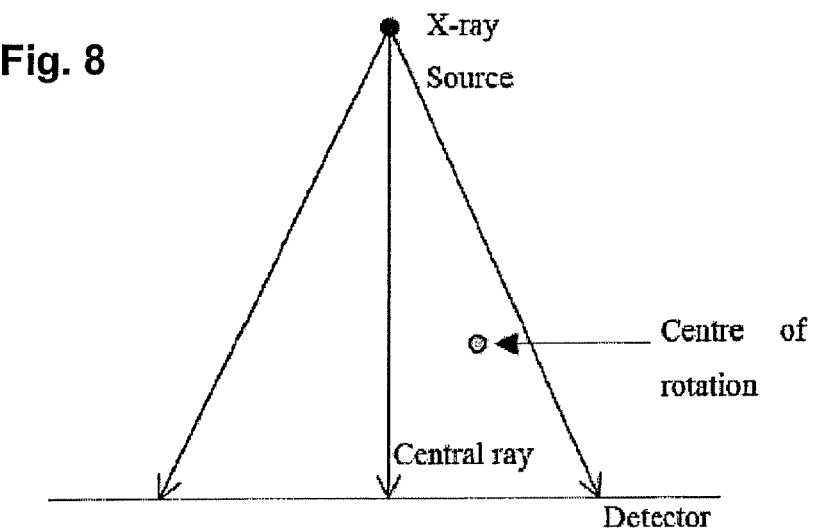
FIG. 8 is a schematic diagram showing the physical geometry of the source and detector of the linear scanning apparatus of FIGS. 1 to 5.

The captured images must be corrected to compensate for the physical geometry of the STATSCAN machine's source-detector pair (i.e. the X-ray source 12 and the detector unit 14 are supported by the C-arm 16). The correction is needed as the midline of the fan beam of X-rays produced by the STATSCAN machine does not fall on the center of rotation of the C-arm system (see FIG. 8). If this is not compensated for then further calculations are unnecessarily complicated.

Figure 9:
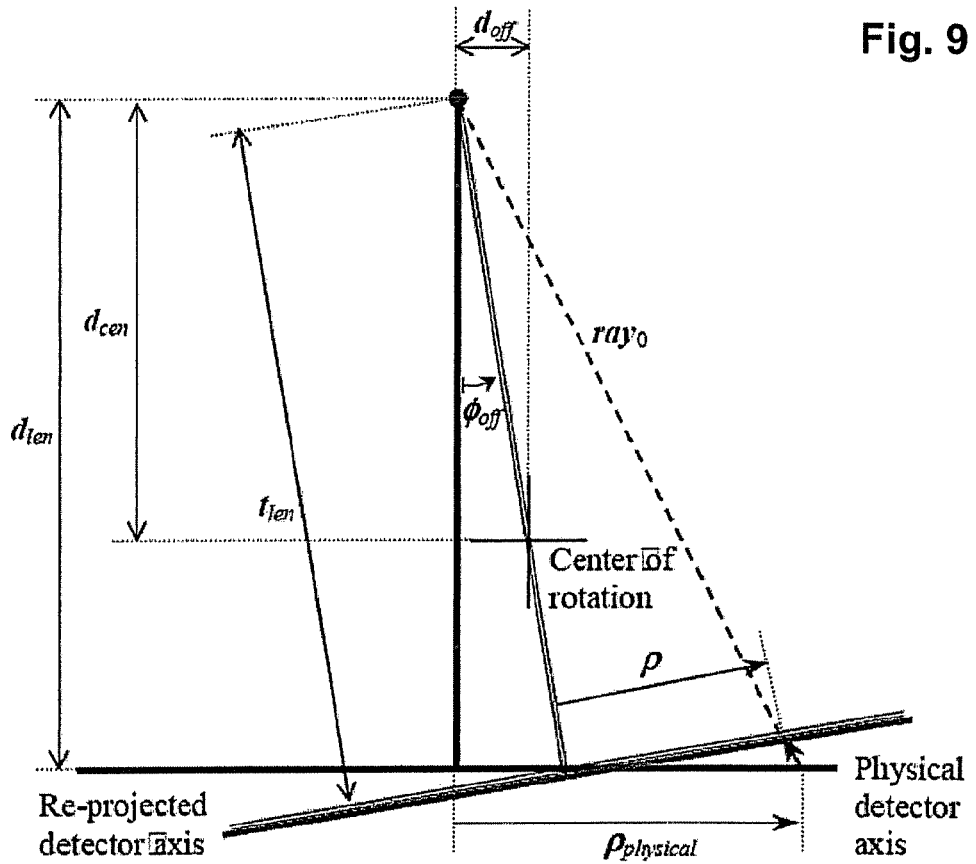
FIG. 9 is a schematic diagram showing the generation of a re-projected fan-beam detector axis according to the method of the invention.

A re-projection of the X-ray data onto a new virtual detector is created. This virtual detector plane has the midline of the fan beam of X-rays passing through the physical center of rotation of the system (see FIG. 9). This new data makes for simpler processing in further stages. Note the highlighted axis, which is the new virtual detector plane created from the original data.

Now for a continuous projection axis $\rho$ and $\rho_{physical}$ the projection values are preserved such that $$P(\rho) = P_{physical}(\rho_{physical}) \qquad \text{Equation 1}$$

where $$\rho = t_{len}\tan\left(\tan^{-1}\left(\frac{\rho_{physical}}{d_{len}}\right) - \phi_{off}\right)$$

$$\phi_{off} = \tan^{-1}\frac{d_{off}}{d_{cen}}$$

$$t_{len} = \frac{d_{len}}{d_{cen}}\sqrt{d_{cen}^2 + d_{off}^2}$$

The values $d_{len}$, $d_{cen}$, and doff are known from measurements taken from the STATSCAN machine. From these all other measurements can be derived. Equation 1 is used to relate points on the physical detector axis $\rho_{physical}$ to points on the re-projected detector axis $\rho$.

However the projector axes are actually discrete instead of continuous, so linear interpolation is used to smooth the data. So the software has taken an original input image and converted it into an equivalent image that would have been taken had the STATSCAN machine had the midline of its fan beam passing through its mechanical centre of rotation.

This process is repeated for every scan taken by the STATSCAN machine to be used in the final undistorted image.

Figure 10:
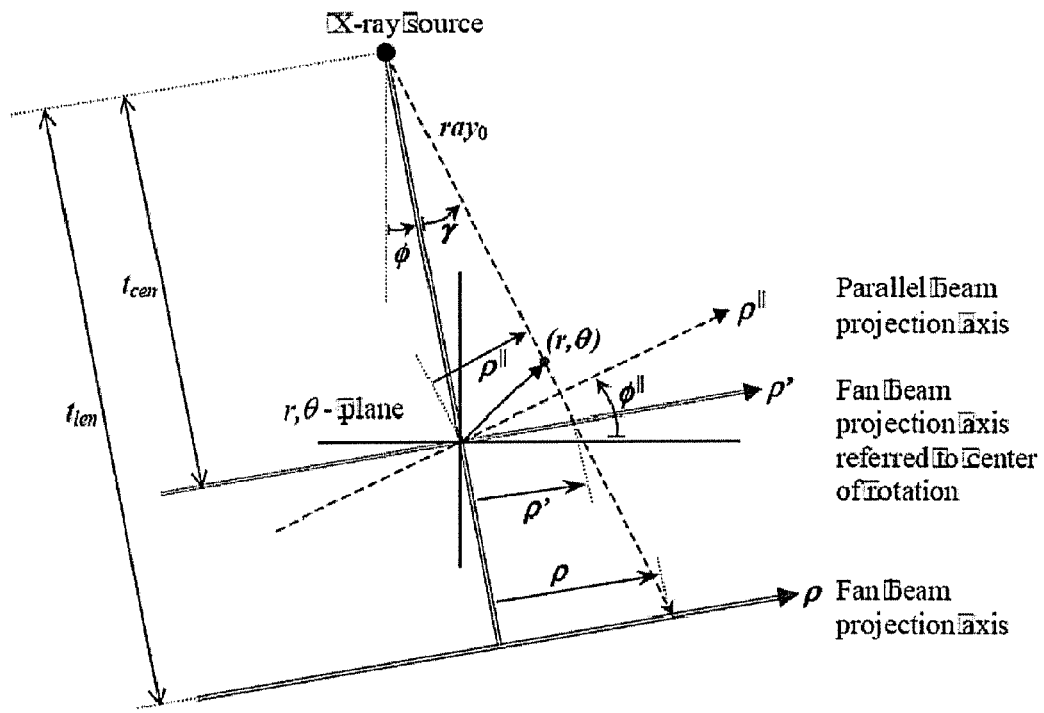
FIG. 10 is a schematic diagram showing the further generation of a virtual parallel beam detector axis according to the method of the invention.

The image is now converted to a virtual parallel beam image. This is done via a re-projection of the fan-beam X-ray data $\rho$ onto a virtual parallel beam detector $\rho^{\|}$ (see FIG. 10), that is to say, the equivalent detector that would have been struck by the X-ray, had it come from a parallel source. This assumes continuous detector axes.

The new data (corrected for the off centre rotation) lies on the Fan Beam Projection Axis ($\rho$). It is convenient to create a new projection of this data referred to the centre of rotation ($\rho'$). From this the information in the Parallel Beam Projection Axis ($\rho^{\|}$) can be extracted in a piece-meal fashion (sometimes called re-binning).

It can be shown that a point on ($\rho'$) has an equivalent point on ($\rho^{\|}$) at a particular angle ($\phi^{\|}$). So a piece of information from a fan-beam projection at a particular angle can be placed onto an equivalent parallel beam projection axis. By combining the information from multiple fan-beam projections it is possible to extract a complete set of parallel beam data for an angle ($\phi^{\|}$).

If we assume the projection values for the different axes are equal where the same ray intersects the axes, i.e.

$$P_\phi(\rho) = P_\phi{'}(\rho') = P_{100}{}^{\|}(\rho')$$

Therefore parallel projection data can be extracted from the fan beam data, using $$\rho^{\|} = \rho' \cos\gamma = \frac{\rho' t_{cen}}{\sqrt{\rho'^2 + t_{cen}^2}}$$

$$\rho' = \rho \frac{t_{cen}}{t_{cen}}$$

$$\phi^{\|} = \phi + \gamma$$

$$\gamma = \tan^{-1}\frac{\rho'}{t_{cen}}$$

These equations can be used to create an equivalent parallel projection axis from the original fan beam projection axis. However the angle of the parallel view $\phi^{\|}$ must be specified at the start.

The next step is to create a sinogram from the available scans. A sinogram is a view of each slice of an image at a specified angle. From all the scans taken of the object of interest we now create a sinogram from each line in the image. It is on this sinogram that the fan beam-to-parallel beam conversion is performed using the equations above.

Figure 13:
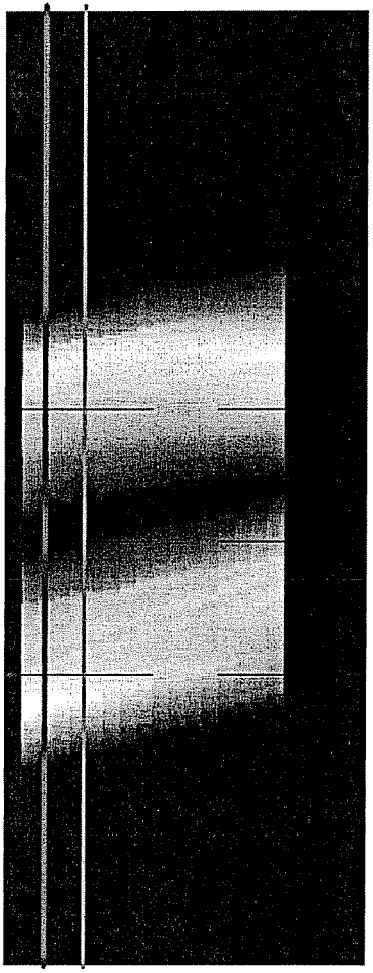
FIG. 13 is a sinogram composite of multiple image slices from the selected image line.

FIG. 13 can be seen to be a composite of multiple scan images. The y-axis is the projection axis and the x-axis is the angle of the slice. For each line of the centre of rotation corrected images we take the same line from each scan and place it into a new sinogram at the angle that the scan was taken at.

Figure 11:
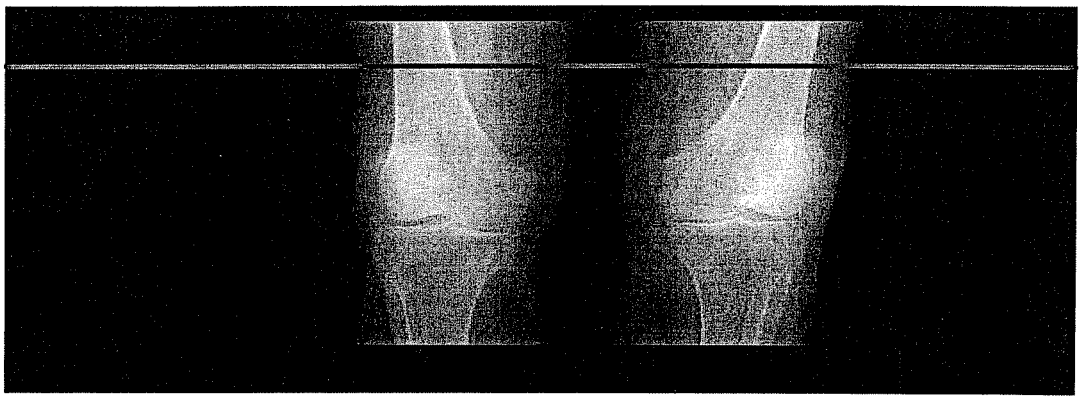
FIGS. 11 and 12 are scans illustrating the use of a selected image line at first and second specified angles.
Figure 12:
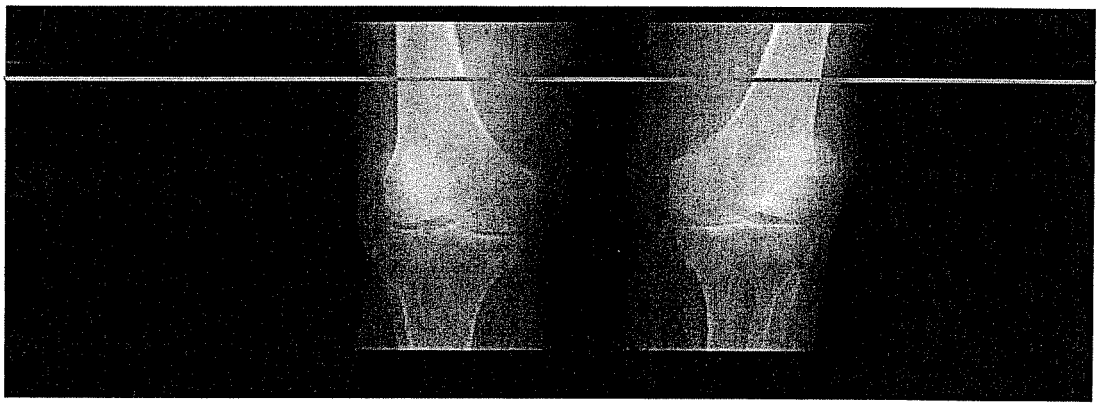

For example, the line 200 (dark grey) of the scan at 02 degrees (FIG. 11) is placed at 02 degrees in the new sinogram. The line 200 (light grey) of the scan at 04 degrees (FIG. 12) is placed at 04 degrees in the new sinogram. Thus this sinogram represents the angular view at line 200 of all our scans. This can then be used to create the parallel beam view of line 200.

The next step is to re-project the sinogram data from a fan to a parallel axis format. Using the relationships from FIG. 10 and the newly constructed sinogram it is possible to reorder the fan beam data into parallel beam data. A new sinogram consisting of parallel beam data is constructed.

Figure 14:
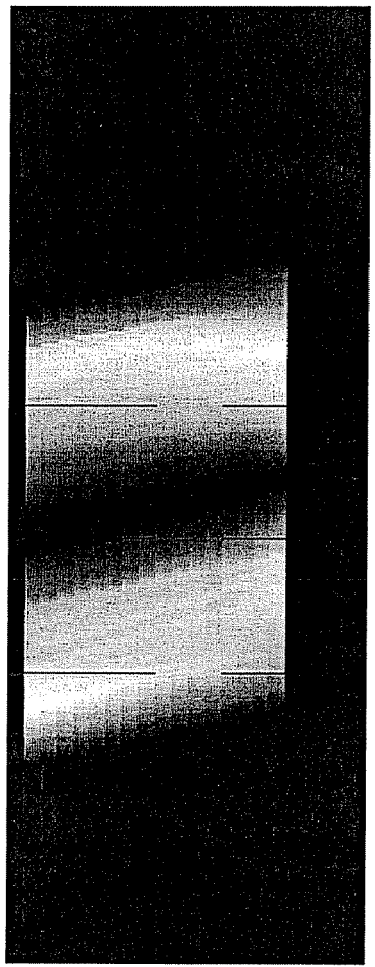
FIG. 14 is a sinogram based on uncorrected fan-beam data.
Figure 15:
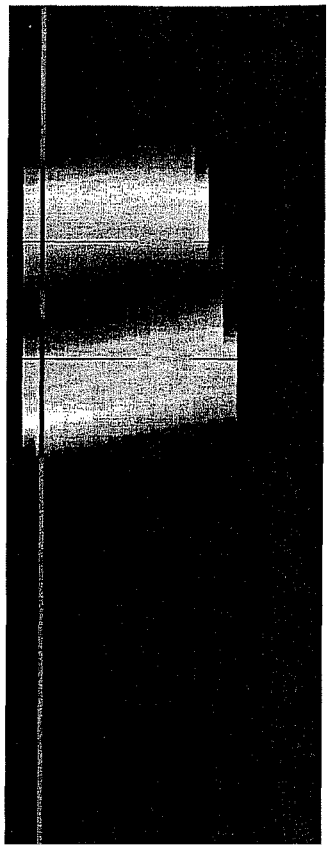
FIG. 15 is a sinogram based on corrected parallel beam data.

The new sinogram that we have created in FIG. 15 (compared with the original fan beam sinogram shown in FIG. 14) from our example represents parallel beam data for line 200 of our scans at a number of angular views. From this sinogram we select the angle that we are interested in and use it to reconstruct our final image. In order to do this we take a slice from our new sinogram at 00 degrees (although it could be at any angle, depending on what we wanted out final view to be) and place it into our new image at line 200.

Figure 16:
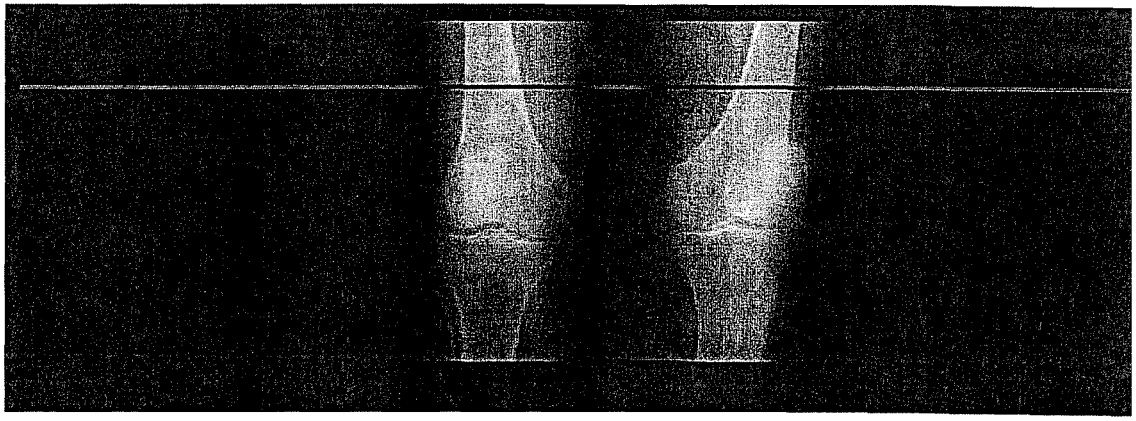
FIG. 16 is a distortion-corrected final image based on the corrected parallel beam data, prepared according to the method of the invention.

This process is repeated for every line in our image until a full reconstruction has been made. FIG. 16 shows the final virtual parallel beam image at 0 degrees.

It can be seen that this new image is equivalent to a parallel beam X-ray image of the object of interest taken at a specific angle of projection. This new image is accurate in both the scanning direction of the C-arm, as well as the beam width direction (i.e. the direction transverse to the scanning direction). Thus, accurate measurements can be made directly from the X-ray image.

Figure 18:
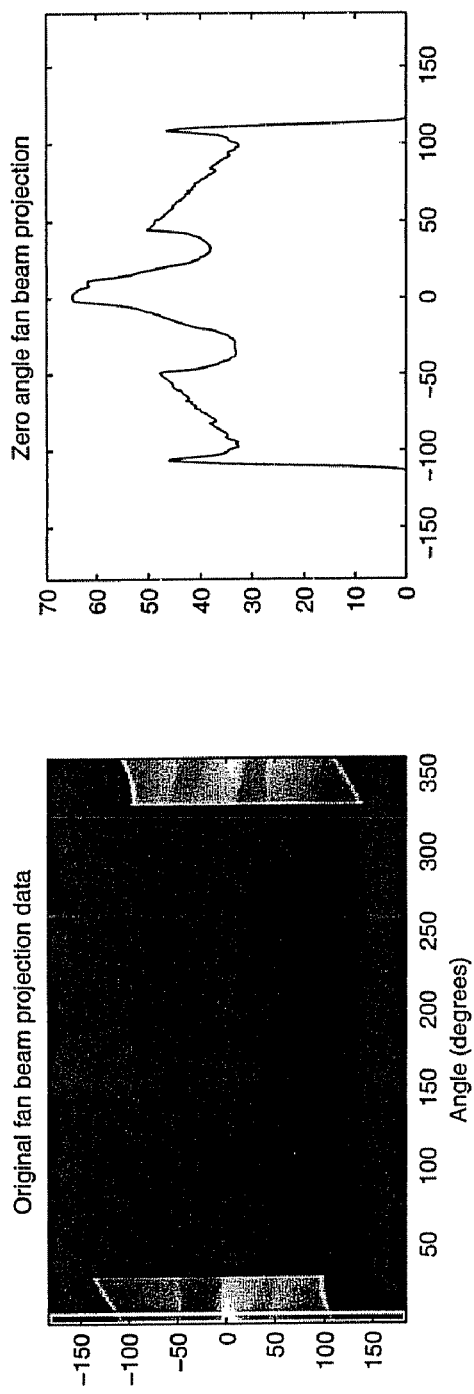
FIG. 18 is a composite diagram showing limited angle fan beam projection data, and a corresponding zero angle profile.
Figure 19:
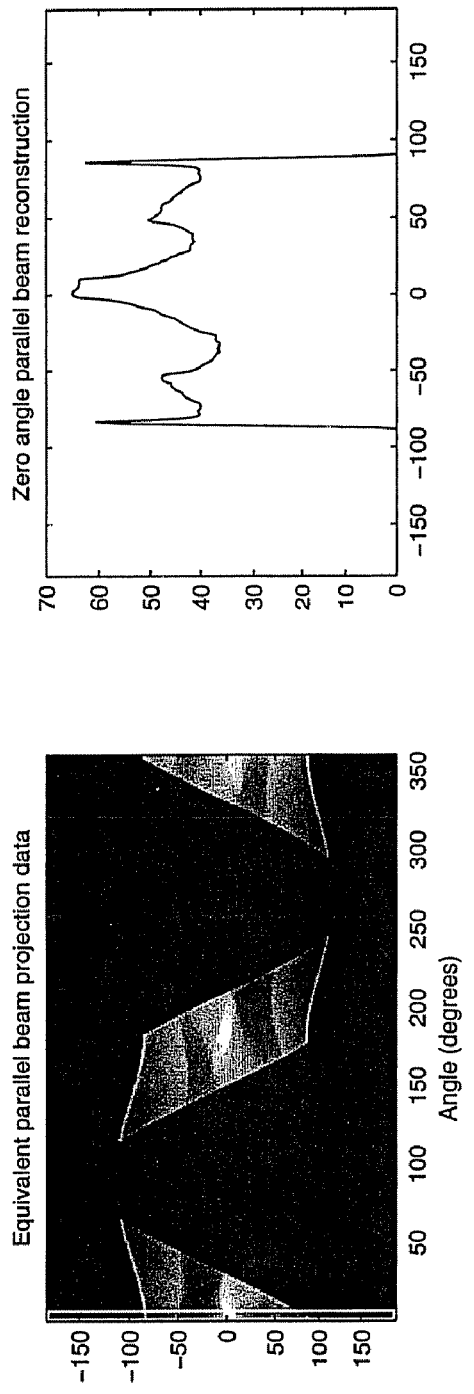
FIG. 19 is a composite diagram showing the limited angle fan beam data remapped to orthogonal projection data, and a corresponding zero angle profile.

FIGS. 18 and 19 are composite diagrams which show the relation between the original and equivalent imaging beams and corresponding profiles. FIG. 18 shows limited angle fan beam projection data and a corresponding zero angle profile, while FIG. 19 shows the limited angle fan beam data remapped to orthogonal projection data, and a corresponding zero angle profile.

Figure 20:
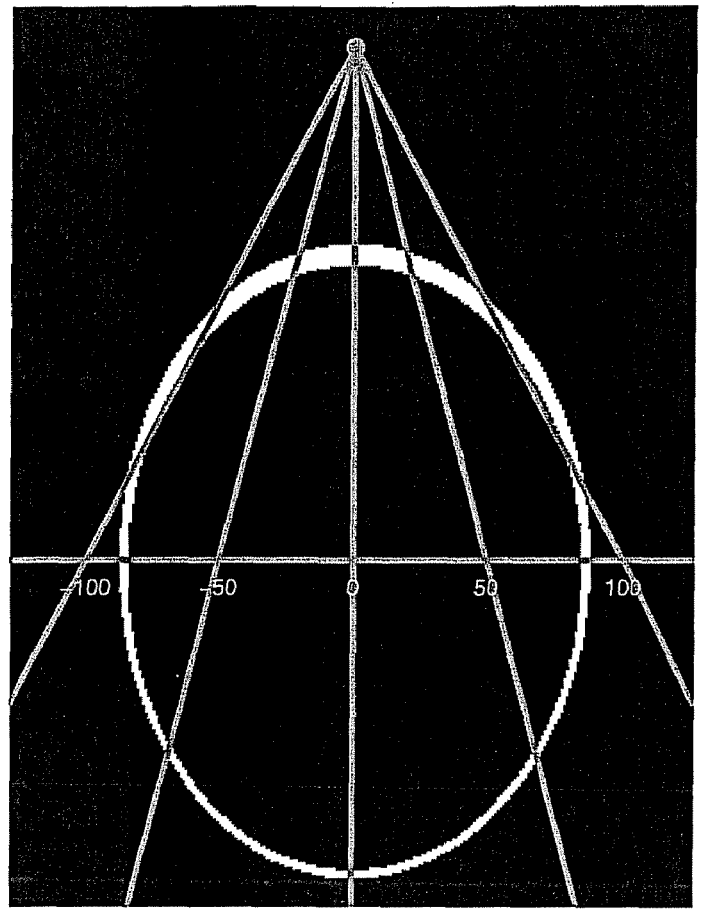
FIG. 20 is a composite diagram showing fan beam projection rays with a distorted zero angle projection profile.
Figure 20:
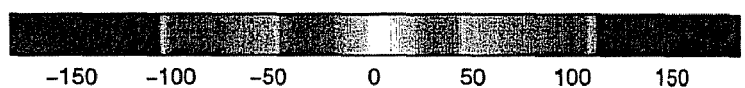
Figure 20:
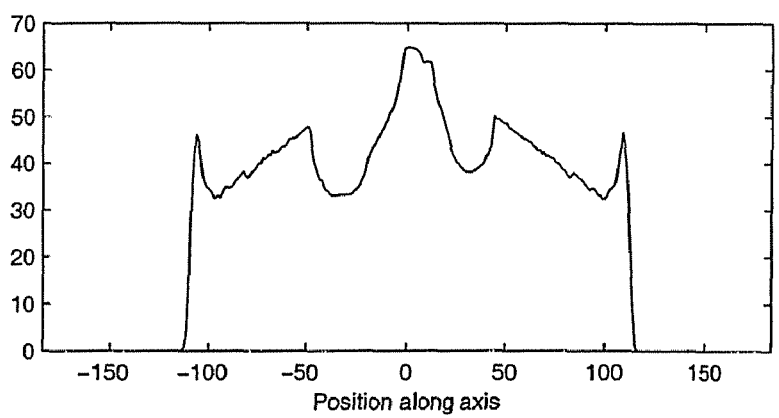
Figure 21:
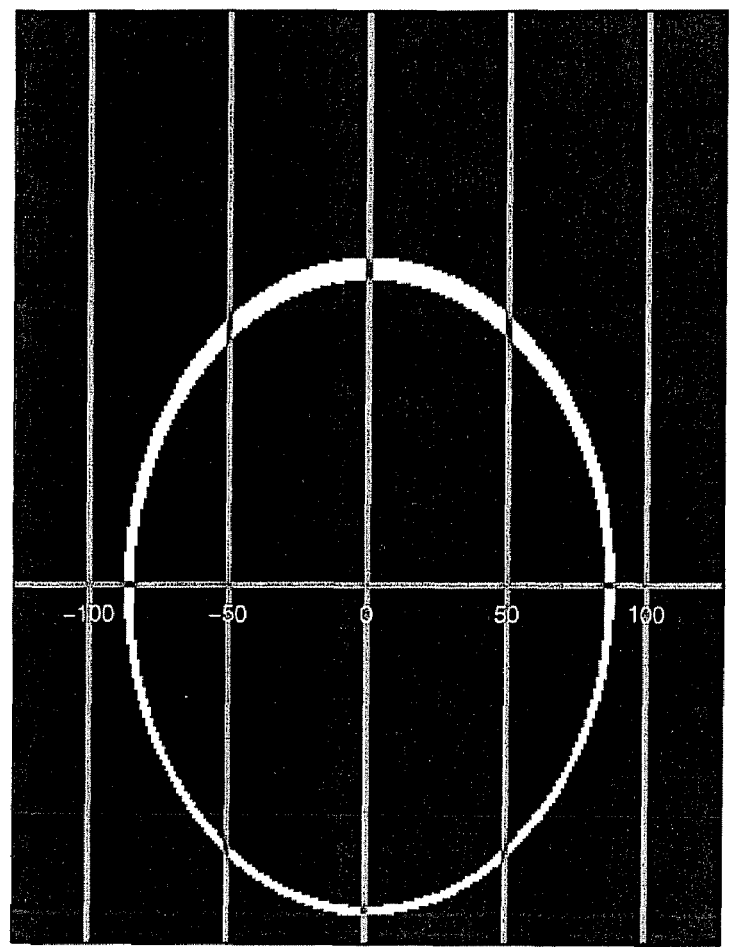
FIG. 21 is a composite diagram showing orthogonal beam projection rays with a corrected zero angle projection profile.
Figure 21:
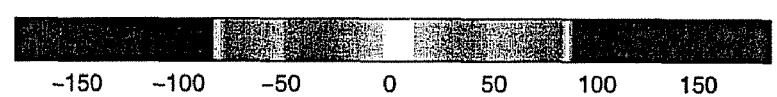
Figure 21:
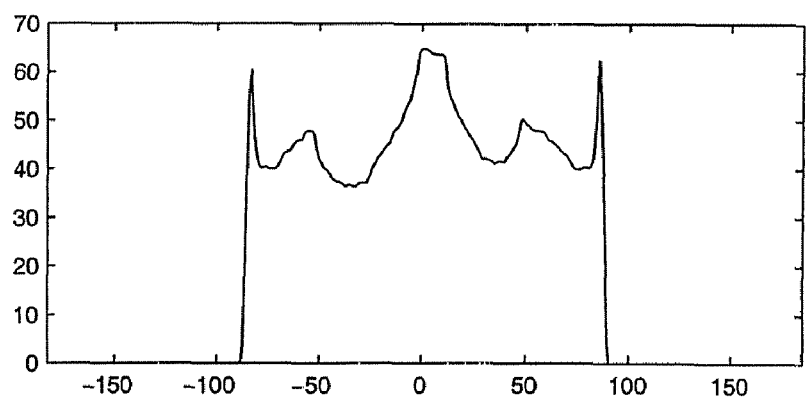

FIGS. 20 and 21 are composite diagrams, the first showing fan beam projection rays with a corresponding distorted zero angle projection profile, and the second showing orthogonal beam projection rays with a corrected zero angle projection profile.

Figure 22:
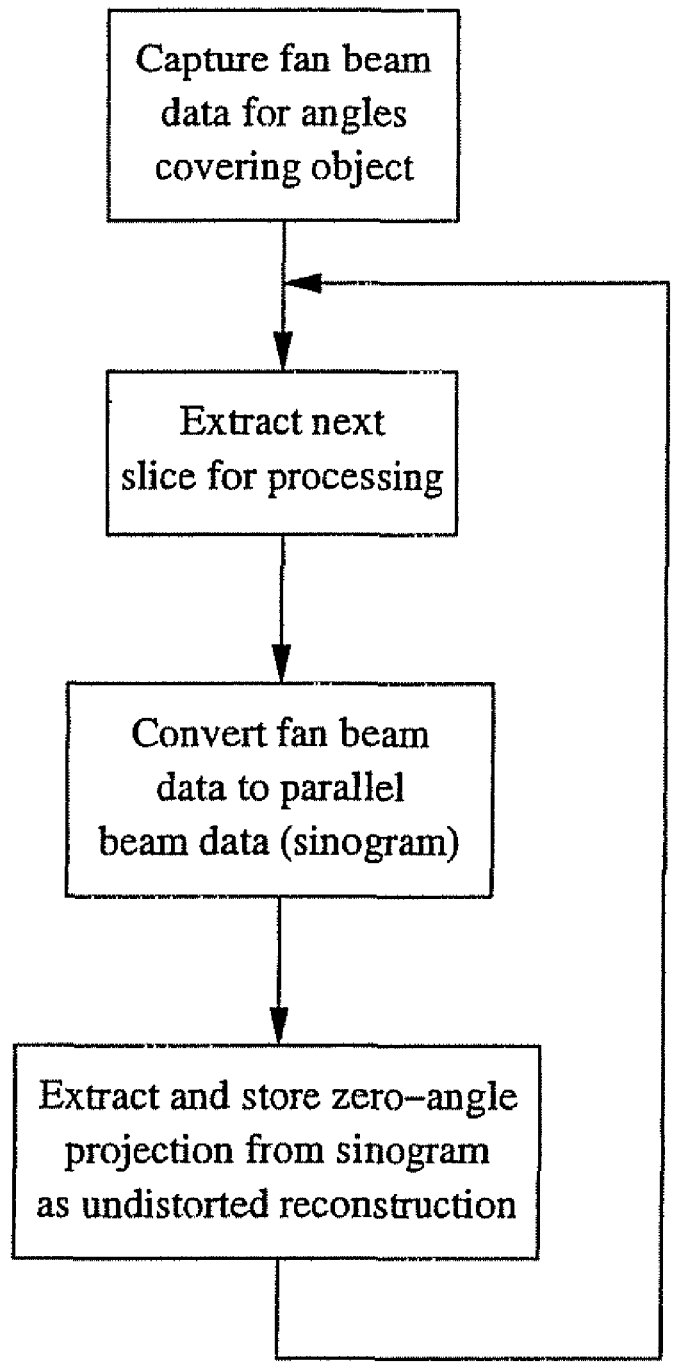
FIG. 22 is a flow chart showing a high-level description of the distortion correction procedure of the invention.
Figure 23:
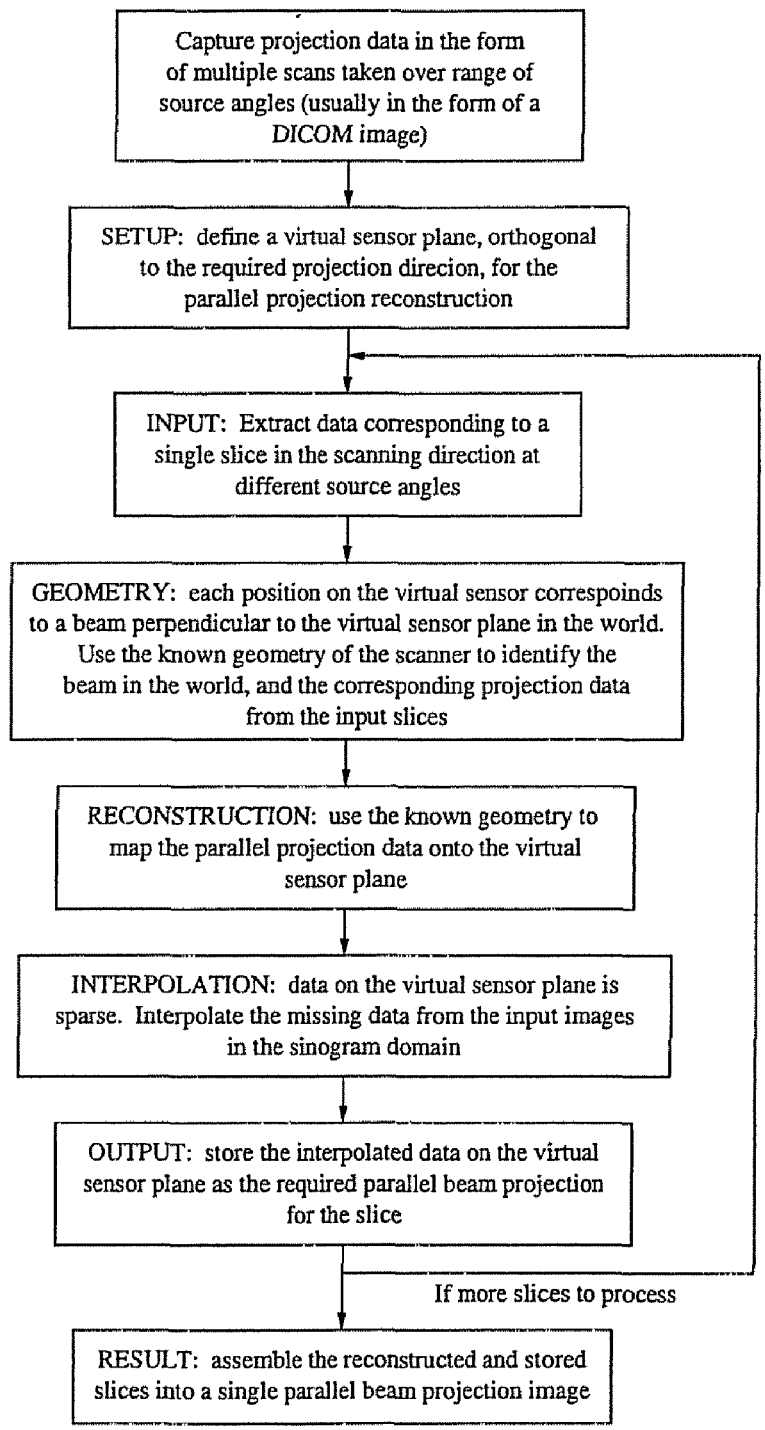
FIG. 23 is a flow chart showing a more detailed description of the distortion correction procedure.

The above described method is summarised in the flow-charts of FIGS. 22 and 23.

It would be useful in some cases to produce similar results with fewer initial fan-beam X-ray data. The above described distortion correction method relies on using the information contained in the fan-beam X-ray data to create a new parallel beam projection. If less than the required amount of fan-beam data is captured, large streaking artefacts will be present in the reconstructed parallel beam image.

Figure 17:
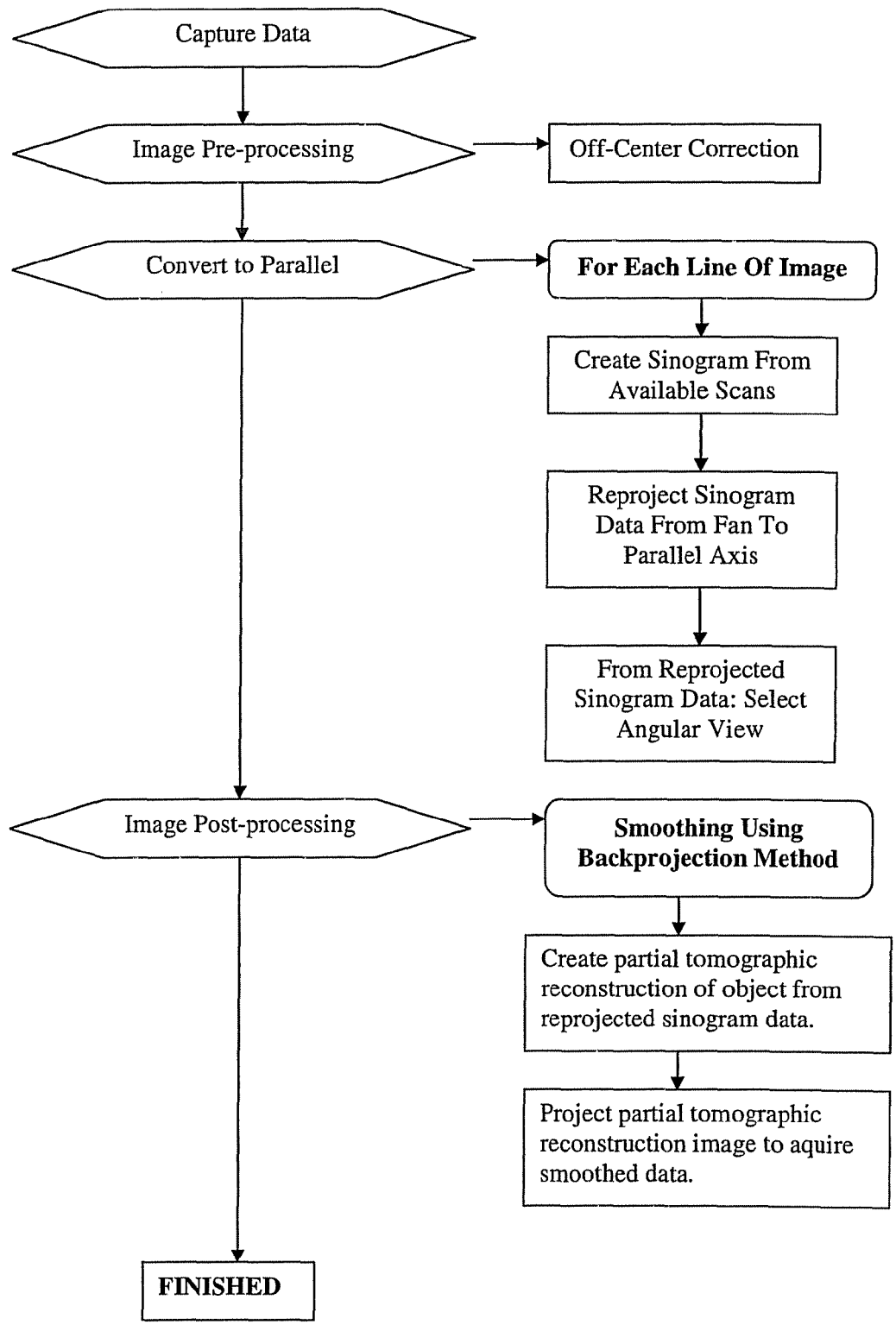
FIG. 17 is a simplified flow chart illustrating major steps in the operation of the method.

In order to deal with this problem, an additional smoothing step is proposed. This involves back-projecting the new parallel beam data and creating a limited partial angle tomographic reconstruction of the object. Thus the back-projection is used to fill in the gaps present in the original data by exploiting the nature of the back-projection method. See the flow chart of FIG. 17 in this regard.

This tomographic reconstruction is then re-projected to create a new, smoother parallel beam image with the streaking artefacts reduced and smoothed. In this way fewer initial scans of the object of interest are required, reducing X-ray exposure and increasing the speed with which the distortion correction can be performed. However, this method is time consuming relative to having taken sufficient initial scans and simply selecting corrected scan lines from their respective sinograms.

The described method produces images from which accurate measurements can be taken. These images are produced from the combination of multiple standard STATSCAN images. The correction can be implemented efficiently on computer and processing time can be minimal, as long as sufficient initial scans are taken and no back-projection post-processing needs to occur.

The invention claimed is:

1. A method of operating imaging apparatus of the kind having a radiation source and an associated radiation detector which are moveable relative to a subject, the method comprising:
   (a) generating a divergent imaging beam from the radiation source;
   (b) moving the radiation source and the radiation detector relative to a subject in a scanning direction to generate output signals from the detector, thereby generating image data containing distortion in a direction transverse to the scanning direction;
   (c) changing the orientation of the radiation source in a direction transverse to the scanning direction and repeating step (b) one or more times to generate a plurality of sets of image data;
   (d) processing each set of image data to obtain equivalent parallel imaging beam data therefrom, corresponding to a given angle in the divergent imaging beam; and
   (e) combining a plurality of said equivalent parallel imaging beam data to generate a synthesized parallel imaging beam image.

2. The method of claim 1 wherein the divergent imaging beam is a fan shaped imaging beam generated by a linear scanning apparatus.

3. The method of claim 2 wherein the fan shaped imaging beam is relatively narrow in the scanning direction and relatively wide in a direction transverse to the scanning direction.

4. The method of claim 2 wherein changing the orientation of the radiation source in a direction transverse to the scanning direction comprises rotating the radiation source and detector about an axis extending parallel to the scanning direction at selected angular intervals.

5. The method of claim 4 wherein the linear scanning apparatus comprises a support member which supports the radiation source and the associated radiation detector for rotation about an axis which extends parallel to the scanning direction, but which is offset relative to a midline of the fan shaped imaging beam, the method including the step of processing the image data to re-project the image data so that it represents a virtual fan shaped imaging beam having a midline that coincides with the axis of rotation of the support member.

6. The method of claim 5 wherein the image data defines a multi-line image, the method comprising generating a set of sinograms from the image data, each sinogram representing angular views at a specified line of the image, reprojecting the sinogram data from a fan bean to a parallel beam format, constructing a set of new sinograms consisting of virtual parallel beam data, and reconstructing a virtual parallel beam image from the virtual parallel beam data at a selected angle of view.

7. Imaging apparatus comprising:
(a) a radiation source arranged to generate a divergent imaging beam and an associated radiation detector;
(b) a first drive arranged to move the radiation source and the detector relative to a subject in a scanning direction to generate output signals from the detector, thereby performing a scan generating image data containing distortion in a direction transverse to the scanning direction;
(c) a second drive arranged to change the orientation of the radiation source in a direction transverse to the scanning direction incrementally between repeated scans, thereby to generate a plurality of sets of image data;
(d) at least one processor for processing each set of image data to obtain equivalent parallel imaging beam data therefrom, corresponding to a given angle in the divergent imaging beam, and for combining a plurality of said equivalent parallel imaging beam data to generate a synthesized parallel imaging beam image; and
(e) a display for generating a visual display of the synthesized parallel imaging beam image.

8. Imaging apparatus according to claim 7 which is a linear scanning apparatus in which the first drive is arranged to move the radiation source and the associated radiation detector along a linear path corresponding to the scanning direction, and wherein the divergent imaging beam is a fan shaped imaging beam.

9. Imaging apparatus according to claim 8 wherein the fan shaped imaging beam is relatively narrow in the scanning direction and relatively wide in a direction transverse to the scanning direction.

10. Imaging apparatus according to claim 8 wherein the second drive is arranged to change the orientation of the radiation source in a direction transverse to the scanning direction by rotating the radiation source and detector about an axis extending parallel to the scanning direction at selected angular intervals.

11. Imaging apparatus according to claim 10 wherein the linear scanning apparatus comprises a support member which supports the radiation source and the associated radiation detector for rotation about an axis which extends parallel to the scanning direction, but which is offset relative to a midline of the fan shaped imaging beam, said at least one processor being operable to apply an algorithm to the image data to re-project the image data so that it represents a virtual fan shaped imaging beam having a midline that coincides with the axis of rotation of the support member.

12. Imaging apparatus according to claim 11 wherein the image data defines a multi-line image, said at least one processor being operable to generate a set of sinograms from the image data, each sinogram representing angular views at a specified line of the image; to reproject the sinogram data from a fan bean to a parallel beam format; to construct a set of new sinograms consisting of virtual parallel beam data; and to reconstruct a virtual parallel beam image from the virtual parallel beam data at a selected angle of view.

* * * * *